US006372260B1

(12) United States Patent
Andersson et al.

(10) Patent No.: US 6,372,260 B1
(45) Date of Patent: Apr. 16, 2002

(54) INCORPORATION OF ACTIVE SUBSTANCES IN CARRIER MATRIXES

(75) Inventors: Marie-Louise Andersson; Catherine Boissier, both of Göteborg; Anne Mari Juppo, Mölndal; Anette Larsson, Olofstorp, all of (SE)

(73) Assignee: AstraZeneca AB, Sodertalje (SE)

( * ) Notice: Subject to any disclaimer, the term of this patent is extended or adjusted under 35 U.S.C. 154(b) by 73 days.

(21) Appl. No.: 09/297,440
(22) PCT Filed: Apr. 9, 1999
(86) PCT No.: PCT/SE99/00583
  § 371 Date: Apr. 30, 1999
  § 102(e) Date: Apr. 30, 1999
(87) PCT Pub. No.: WO99/52507
  PCT Pub. Date: Oct. 21, 1999

(30) Foreign Application Priority Data

Apr. 14, 1998 (SE) .............................. 9801287

(51) Int. Cl.[7] .............. A61K 9/50; A61K 9/48; A61K 9/20; B01J 13/02; B32B 5/16

(52) U.S. Cl. .............. 424/501; 424/451; 424/464; 424/502; 264/4.3; 264/4.33; 264/4.6; 428/402.21
(58) Field of Search ............. 424/501, 502, 424/4.3, 451, 464; 264/4.33, 4.6; 428/402.21

(56) References Cited

FOREIGN PATENT DOCUMENTS

EP  0677332  10/1995

OTHER PUBLICATIONS

Chemical Abstracts, vol. 126, Nov. 14, Apr. 7, 1997, (Columbus, Ohio, USA), Gerber, P. et al, "Solids formation by rapid expansion of supercritical solutions", The Abstract No. 187774, Process Technol. Proc. 1996, 12, 369–372.

*Primary Examiner*—Carlos Azpuru
(74) *Attorney, Agent, or Firm*—White & Case LLP

(57) ABSTRACT

A process for the incorporation of an active substance in a carrier system by forming an emulsion of the components and precipitating the system by the use of fluid gas technique.

41 Claims, No Drawings

INCORPORATION OF ACTIVE SUBSTANCES IN CARRIER MATRIXES

FIELD OF INVENTION

The present invention relates to a process for the preparation of a formulation which comprises an active substance associated with a carrier by forming an emulsion of the components and precipitating the system by using a fluid gas technique. The invention also relates to the formulation obtained by this process.

BACKGROUND OF THE INVENTION

Several solutions to the problem of incorporation of active substances in carrier matrixes in order to obtain particle systems have been suggested. Such systems can be utilized in, for instance, immediate release formulations, modified release formulations, extended release formulations, pulsed release formulations, etcetera.

Some examples of such techniques are:
- hot melt microencapsulation (Schwope et al *Life Sci.* 1975, 17,1877)
- interfacial polymerisation (Birrenbach and Speiser, *J. Pharm.Sci.* 1976, 65, 1763, Thies, *In Encyclopedia of Chemical Technology*, 4 ed. Ed. Kirk-Othmer, 1996, 16, p. 632)
- solvent evaporation methods (Cleland, In Vaccine Design. *The subunit and adjuvant approach*, Eds: Powell and Newman Plenum Press, New York; 1995, 439)
- solvent extraction (Cleland, In Vaccine Design. *The subunit and adjuvant approach*, Eds: Powell and Newman Plenum Press, New York; 1995, 439)
- spray drying (WO 94/15636)

An important step in the preparation of such systems is the incorporation step of the active substance. The choice of preparation method for the release system depends on the kind of active substance that is going to be incorporated and the desired release properties of the active substance from the delivery system. All techniques listed above have their advantages and disadvantages. Thus, the hot melt microencapsulation method is unsuitable for thermosensitive active substances. A drawback with the interfacial polymerisation method is that the highly reactive monomers in the water immiscible solvent can react both with the core material and with the encapsulated active substance. A drawback with the solvent evaporation process method is that the method is time consuming and that it only can be performed batch wise. As in the solvent evaporation technique, the extraction method is also time-consuming as it can only be performed batch wise. A drawback with the spray drying method is that it is difficult to produce particles in the nanometer size range. This method is also unsuitable for thermosensitive substances or oxidative sensitive active substances because of the exposure of heat and air in the process.

Supercritical fluid technology has advanced in the recent years. Briefly, a supercritical fluid can be defined as a fluid at or above its critical pressure and critical temperature simultaneously. The physicochemical properties of supercritical fluids are flexible with temperature and pressure and could be selected to suit a given application. There are several new techniques used today, one is known as rapid expansion of supercritical solutions (RESS) and another is known as gas anti-solvent precipitation (GAS). In the GAS technique a substance of interest is dissolved in a conventional solvent, a super-critical fluid such as carbon dioxide is introduced into the solution, leading to a rapid expansion of the volume of the solution. As a result, the solvent power decreases dramatically over a short period of time, triggering the precipitation of particles. Cf J. W. Tom and P. G. Debenedetti in J. Aerosol Sci., 22 (1991), 555–584; P. G. Debenedetti et al in J. Controlled Release, 24 (1993), 27–44 and J. W. Tom et al in ACS Symp Ser 514 (1993) 238–257; EP 437 451 (Upjohn) and EP 322 687 (Schwarz Pharma). A modification of the GAS system has recently been developed (WO 95/01221 and WO 96/00610). It is called the SEDS (solution enhanced dispersion by supercritical fluid) process, which utilises supercritical fluid technologies for particle formation.

Protein can be incorporated in the carrier matrixes, like other active substances, using the encapsulation methods listed above. The protein is dissolved in a water phase, suspended or directly dissolved in the phase containing the carrier. A disadvantage with proteins dissolved in organic solvents is the low solubility of proteins in organic solvents and / supercritical fluids/modified supercritical flows (Stahl et al, "Dense Gas Results", *Fluid Phase Equilibra*, 1983, 10, 269). Another disadvantage with the protein directly dissolved or suspended in the organic solvent is that the organic solvent may unfold or denature the protein. (Dill and Shortle *Ann. Rev. Biochem.*, 1991, 60, 795–825). This may lead to a loss of therapeutic effect, e.g. inmunological effect.

In supercritical fluid techniques, the proteins have been dissolved directly-in DMSO for preparation of pure protein particles (Winters et al., *J.Pharm.Sci.*, 1996, 85, 586–594 and *Pharm.Res.*, 1997, 14, 1370–1378) or in co-precipitation with polymer, with both, the polymer and the protein, dissolved in DMSO (WO9629998 and Bertucco et al. *In High Pressure Chemical Engineering*, 1996, 217–222). Even a mixture of ethanol and water has been used as a solvent for a protein and a polymer in SAS (EP0542314 and Tom et al., *In Supercritical Fluid Engineering Science*, ACS Symposium Series, 1993, 514, 238–257).

Protein particles have been prepared from water solution in the SEDS technique using a three-component nozzle, where the protein solution in water is first co-introduced with ethanol and then mixed with supercritical carbon dioxide (WO9600610) in the nozzle. Even if the contact time between[]the aqueous solution and the ethanol is very short, it may cause destruction of the protein conformation.

Low molecular weight substances have also been co-precipitated with polymers with supercritical fluid techniques. In EP322687 is presented the preparation of a drug form which comprises an active substance and carrier with anti-solvent technique and with RESS (Kim et al. *Biotechnol Prog* 1996, 12, 650–661, Chou and Tomasko, *The 4$^{th}$Int.Symp. on Supercritical Fluids*, Sendai, Japan, 1997, 55). Here, in the anti-solvent technique, the active substance and carrier are dissolved or dispersed in the same liquid medium and combined with supercritical fluid. Examples include in these documents only refer to incorporation of hydrophobic compounds in L-PLA spheres. Nothing about the compounds in aqueous phase was mentioned, as well as, in other studies reported on PCA (Bodmeier et al., *Pharm.Res.*, 1995, 12, 1211–1217), SAS (Bertucco et al. *In High Pressure Chemical Engineering*, 1996,217–222), GAS (Chou and Tomasko, *The 4$^{th}$Int.Symp. on Supercritical Fluids*, Sendai, Japan, 1997,55) or ASES (Bleich and M üller, *J. Microencapsulation*, 1996,13, 131–139).

DISCLOSURE OF THE INVENTION

It has now been found that it is possible to associate an active substance or substances with a carrier system by forming an emulsion of the components and precipitating the system by using a fluid gas technique. The active substance or active substances are incorporated within and/or around the carrier system, which includes that the carrier can also surround the active substance or active substances.

This improved method for preparing active substance containing carrier systems is based on the use of emulsions. The emulsion is a mixture of two non-miscible liquids, or phases, where one liquid is finely dispersed in another liquid One of the liquids is.more polar, for instance water or aqueous phase, in comparison to the other liquid, for instance an organic solvent or a mixture of solvents (oil phase, here called the non-aqueous phase). The emulsion can be either kinetically stable (macroemulsion) or a thermodynamically stable (microemulsion), or combination thereof. In order to stabilise the emulsion an emulsifier, either alone or in combination with other emulsifiers, such as but not limited to, surfactants, polymers, lipids can be used. The emulsifiers are dissolved in either the aqueous phase and/or the non-aqueous phase. The active substance or substances, which is/are going to be incorporated or/and associated to the carrier system, are dissolved, suspended or solubilized in the aqueous phase. The carrier material is either dissolved in the non-aqueous phase or the aqueous phase. The aqueous phase is emulsified in an non-aqueous phase, or vice versa.

The non-ionic surfactants can be, but are not limited to: polyoxyethylene sorbitan fatty acid esters, sorbitan fatty acid esters, polyoxyethylene alkyl ethers, sucrose esters and n-octyl-b,D-glycopyranoside(n-OG).

The anionic surfactants can be, but are not limited to: sodium dodecyl sulphate, sodium 1,4-bis(2-ethylhexyl) sulphosuccinate (AOT) and salts of fatty acids.

The cationic surfactants can be, but are not limited to: alkyltrimethylammonium salts and dialkyldimethylammonium salts.

The zwitterionic surfactants can be, but are not limited to: 3((3 -cholamidopropyl)dimethylammonio)-1-propane sulphonate, dodecyl-N-betaine.

The polymeric emulsifiers can be, but are not limited to: poly(vinyl pyrrolidone), polyglycerol polyricinoleate, poly(vinyl alcohol) and block copolymers.

The lipid emulsifiers can be, but are not limited to: cholesterol, phosphatidylcholine, phosphatidylethanolamine and phosphatidic acid.

In this invention, the aqueous phase is defined to be aqueous solutions (non-miscible with the non-aqueous phase) and/or other solutions which are non-miscible with the non-aqueous phase and more polar than the non-aqueous phase.

The non-aqueous phase comprises, but is not limited to, conventional organic solvents, like methylene chloride, chloroform ethylacetate, or mixtures of organic solvents.

The carrier material can be, but is not limited to, polymers, fillers, disintegrants, binders, solubility enhancers and other excipients, and combinations thereof.

The polymers may be synthetic or of natural origin. They may be biodegradable or not, e.g. polystyrene. Groups of polymers that can be used as carriers are, but not limited to, polysaccharides, polyesters, polyethers, polyanhydrides and polypeptides.

Examples of polysaccharides are, but not limited to, celluloses, hydroxypropyhnethylcellulose (HPMC), ethylcellulose (EC), pectin, alginates, chitosan, agar, hydroxyethylcellulose (HEC), xanthan, ethylhydroxyethylcellulose (EHEC).

Examples of polyesters are, but not limited to, polylactide (PLA), polyglycolide (PGA), copolymers of these (PLG), polyhydroxybutyrate (PHB) and polycaprolactone.

Examples of polyethers are, but not limited thereto, polyethyleneoxide and polypropyleneoxide.

Examples of polyanhydrides are, but not limited to, poly(sebacic acid), poly(carbophenoxypropane), poly (fiimaric acid) or copolymers of these.

Examples of active substance are medicinal agents, toxins, insecticides, viruses, diagnostic aids, agricultural chemicals, commercial chemicals, fine chemicals, food items, dyes; explosives, paints, polymers, or cosmetics etc. The active substances may have a high molecular weight (defined herein as more than 5.000 Dalton) such as, but not limited to, proteins, antigens, such as a Helicobacter antigen, polypeptides, polynucleic acids, polysaccharides or a low molecular weight (defined herein as 5.000 Dalton or less) such as, but not limited to, Bodipy®. The enzyme activity and the immunogenic activity of the proteins can be maintained by using the process according to the invention.

Here the definition of fluid gas includes material in its supercritical and near-supercritical state as well as compressed gases. The supercritical fluid can be, but not limited to, carbon dioxide, nitrous oxide, sulphur hexafluoride, xenon, ethylene, chlorotrifluoromethane, ethane and tifluoromethane. Near-supercritical state is herein defined as the state where the pressure and/or temperature are below the critical values. For instance, the lower limit for the near-supercritical state regarding carbon dioxide is 0.65 Tc (critical temperature) and for propane 0.30 $T_c$.

The emulsion system described might contain one or more additives, such as, but not limited to:

buffers, e g phosphate, carbonate, tris(hydroxymethyl) aminomethane (TRIS) etc.

substances for increasing the chemical and/or physical stability for the substance, e g trehalose and polyethyleneglycol (PEG);

adjuvants to further enhance the effect of the active substance, e g immunological response stimulators like lipid A and its derivatives, cholera toxin (CT), or absorption enhancers e g mono- or diglyceriders, fatty acids, bile salts or enzyme inhibitors e g aprotonin, ethylenediaminetetraacetic acid, polyacryl acid, or adjuvants for active substance targeting e g antibodies;

solubilisation agents, like n-octyl-b,D-glycopyranoside (n-OG).

The present invention can briefly be described as a process for the preparation of a formulation which comprises an active substance or active substances associated with a carrier characterized in that an emulsion is prepared by mixing a liquid, non-aqueous phase and a liquid, aqueous phase, the aqueous phase comprising the active substance or active substances and the carrier being present in at least one of the phases, the emulsion is contacted with a fluid gas using an anti-solvent technique, units freed of liquid phase are obtained.

The process chosen for manufacturing the carrier system is exemplified by the following general description, and in the Experimental Section below.

In general, these procedures are based on the formation of the carrier system in the following steps:

preparing an aqueous phase containing the active substance or substances, preparing a non-aqueous phase(s) (non-miscible with the aqueous phase), dissolving the carrier material, emulsifier and/or additives in the non-aqueous phase and/or aqueous phase formation of the emulsion composed of at least an aqueous phase and a non-aqueous phase;

using the fluid gas technique to form the carrier system with the active substance.

The first step can be carried out by dissolving, dispersing and/or solubilising the active substance or substances in an aqueous phase.

The fourth step can be carried out using different techniques for emulsification like e g homogenisation, ultra sonic and high pressure homogenisation. The microemulsion or the macroemulsion can also be a so-called double emulsion where the non-aqueous phase is dispersed in the aqueous phase (containing the active substance(s)) which is dispersed in another non-aquoeous phase or where the aqueous (containing the active substance(s)) is dispersed in the non-aqueous phase which is dispersed in another aqueous phase.

In the fifth step the fluid gas technique used for formation of the carrier systems with the active substance is an anti-solvent technique such as, but not limited to, a solution enhanced dispersion by supercritical fluid technique (SEDS), an aerosol solvent extraction system technique (ASES), a supercritical anti-solvent technique (SAS), a gas anti-solvent precipitation technique (GAS) or a precipitation with compressed fluid anti-solvent technique (PCA). If the aqueous phase is the outermost phase in the macroemulsion or microemulsion, a modifier might be needed to be mixed with the fluid gas or to be co-introduced with the emulsion just before contact with the fluid gas. This modifier is an organic solvent such as, but not limited to, ethanol and acetone.

The carrier system containing the active substance(s) according to the invention can be used for pharmaceutical purposes like, but not limited to, therapeutic, prophylactic and diagnostic purposes.

When the invention refers to pharmaceutical applications the active substance-loaded carrier system can be given by different administration routes, such as, but not limited to, by the oral, the rectal, the tonsillar, the buccal, the nasal, the vaginal, the parenteral, the intramuscular, the subcutaneous, the intraocular, the pulmonary, the transdermal, the inplantate, or the intravenous etc. administration route.

The pharmaceutical dosage form prepared with this technique used may be a solid, semisolid, or liquid dispersion prepared by use of well known pharmaceutical techniques, such as blending, granulation, compression, coating, etc. Further, the formulations may be monolithic, such as tablets, or capsules, or in the form of multiple formulations administered in a tablet, capsule or sachet.

The droplet size can be affected by the emulsifiers because the emulsifiers may be dissolved in the continuous phase to some extent. Normally the emulsifiers decrease the surface energy, which contributes to a decrease in the droplet size.

The emulsifiers can affect the agglomeration of carrier systems because they may be located in the droplet/supercritical interface. When the droplet is transformed to a carrier system, the emulsifiers may still be located on the surface of the carrier system. Thereby, the location of the emulsifier on the surface or the carrier system may decrease the degree of agglomeration of the carrier system formed, as has been previously described for polymer particles (Mawson et al., Macromolecules, 1997, 30, 71).

Furthermore, the emulsifiers for the emulsion, that are incorporated in the carrier system as well as the substance or the substances, might improve the characteristics release from the carrier system by e.g., but not limited to, solubilisation of the substance and faster water penetration in the carrier system.

EXPERIMENTAL SECTION

Materials and Methods

In this section, the materials, analytical methods and preparation techniques used in the following examples are described.

Poly(3-hydroxybutyrate) (PHB, Astra Tech, Sweden, molecular weight (MW) 63 500 g/mol) or poly(DL-lactic-co-glycolic acid) 50:50 (PLG RG 502 H, Boehringer Ingelheim, Germany, MW 6000 g/mol) were used as carrier materials. n-Octyl-β-D-glucopyranoside (n-OG, Sigma, Mo., U.S.A.), poly(vinylpyrrolidone) (PVP, Aldrich, Germany, MW 10 000 g/mol) and sodium 1,4-bis(2-ethylhexyl) sulphosuccinate (AOT, Sigma, Mo., U.S.A.) were used as stabilisers. Methylene chloride (99.5%) was used as a solvent and carbon dioxide as a supercritical fluid. Ethanol (99.5%) was used as a modifier in supercritical processing.

Two different proteins were used: highly water soluble carbonic anhydrase (CA, Sigma, Mo., U.S.A.) and a lipidated, water insoluble Helicobacter pylori adhesion protein A in stock solution (HpaA, CSL, Australia). A fluorescent substance used as a low molecular weight model substance was Bodipy® (D3238, Molecular Probes Europe, Holland).

In the protein analysis the SDS laemmli reagent solution was prepared by diluting to one fourth from the stock solution consisting of 1.25 ml TRIS HCl 2 M (pH 6.8) buffer solution, 5.05 g glycerol (99%), 0.8 g sodium dodecylsulphate (SDS), 1 ml 2-mercaptoethanol, 1 µl bromophenol blue and 10 ml water.

Analysis of Particles

The particle size, form and morphology were studied with scanning electron microscopy.

Determination of Active Substance Loading

PHB Particles a) Total Protein Content:

Particles (3–10 mg) were dissolved in 300 µl chloroform. SDS-laemmli (400 µl) was then added and the protein was extracted from the organic phase to the water phase. The samples were shaken at 60° C. for 30 min. The water phase was heated to 95° C. for 15 min and the protein content analysed by polyacrylamide gel electrophoresis (SDS-PAGE).

b) Bodipy® content.

Water (5 ml) was added to 2 mg of particles containing Bodipy® (particles not dissolved). Bodipy® was released from the particles and the concentration was determined spectroscopically (absorptivity 97 000 MT$^-$ cm$^3$ GBC UV/VIS 920, Australia).

PLG Particles a) Total Protein Content:

To the PLG particles (3–10 mg), 1 ml of acetone was added. The polymer dissolved, whereas the protein precipitated. The protein precipitate was centrifuged for 15 minutes at 17 530×g, and about ⅔ of the supernatant was removed with a Hamilton syringe. Pure acetone (1 ml) was added in order to wash the precipitate twice. The remaining acetone was evaporated by vacuum centrifugation. SDS-Laemmli (200 μl) was added and the sample was heated to 95° C. for 15 minutes. The analysis of the protein content was performed by SDS-PAGE.

b) Analysis of the Amount of the Surface Associated Protein:

Analysis of the amount of protein associated to the surface was performed according to Rafati et al. (*Journal of Controlled Release* 1997 43, 89–102). To 5–6 mg of the PLG particles 2 ml of 2% (w/v) SDS in water was added. The samples were shaken for 4 hours. The samples were then centrifuged at 2700×g for 3 minutes and the supernatant removed to a new tube. The water was evaporated by vacuum centrifuigation and 1 ml Laemmli (without SDS) was added. The water phase was heated to 95° C. for 15 min and the protein amount analysed by SDS-PAGE.

Preparation of Particles

Particles were prepared in a SEDS equipment (Bradford Particle Design, Bradford, UK) from the emulsion containing the active substance and the carrier (WO9501221 and WO9600610).

The emulsion and the antisolvent ($CO_2$) were introduced into a coaxial nozzle, which was located inside a pressure vessel which was located in an oven. Under controlled pressure and temperature conditions, the antisolvent extracts the solvent from the formed emulsion droplets. The concentration of the carrier in the droplets is thereby increased, leading to rapid particle formation. The particles were collected in a vessel, while the antisolvent and the extracted solvent emerged through a back pressure regulator.

The nozzle used was a three component nozzle connected, either in a sandwich mode or in a two-solutions mode, with an opening of 0.2 mm in diameter. In the sandwich mode, the supercritical fluid passes through the inner-most and the outer-most passage, while the emulsion passes through the intermediate passage. In the two solution mode, the emulsion and the modifier like e.g. ethanol are mixed just before contact with the supercritical fluid. The supercritical fluid passes through the outer passage, the modifier through the intermediate passage and the emulsion through the inner passage.

EXAMPLE 1

HpaA in PHB, Water Content of the Emulsion: 20% (v/v)

PHB was dissolved in methylene chloride at 2 bar, 90° C. Equal volumes of 2% (w/w) PVP (aq) and HpaA stock solution [1.11 mg/ml HpaA in TRIS-HCl buffer; (10 mM, pH 8) and 2% (w/w) n-OG] were mixed. This mixture (3.8 ml) was injected (during homogenisation at 20000 rpm) to 15.2 ml methylene chloride containing of 1% (w/w) PHB and 0.4% (w/w) AOT in a 25 ml Kinematica dispersion vessel. The total homogenisation time was 3 minutes. The homogenizer used was a Polytron PT3100, Rotor PT-DA 3012/2 (Kinematica AG, Switzerland). All procedures were performed under ambient conditions.

Two runs were made from this emulsion with different rning conditions in the SEDS equipment. The run 1 was done by using the three-component nozzle in the two solution mode with ethanol (flow rate 0.5 ml/min) as a modifier. In run 2 the sandwich mode was used (Table 1).

TABLE 1

SEDS processing of emulsion in example 1

| Run | Modifier | P (bar) | T (° C.) | Flow rate $CO_2$ (ml/min) | Flow rate emulsion (ml/min) |
|-----|----------|---------|----------|---------------------------|------------------------------|
| 1   | ethanol  | 180     | 50       | 26                        | 0.1                          |
| 2   | —        | 240     | 35       | 26                        | 0.1                          |

According to SEM graphs, the particle size was 1–3 μm for both trials (run 1 and run 2).

Theoretical composition of particles should be 55.8% (w/w) PHB, 43.5% (w/w) surfactants 0.6% (w/w) HpaA. The analysis of the total amount of HpaA in the particles gave a result of 0.4% HpaA for both run 1 and run 2.

EXAMPLE 2

Bodipy® in PHB, Water Content of the Emulsion: 33% (v/v)

The purpose was to associate a low molecular weight molecule to the carrier matrix using an emulsion with 33% (v/v) water content. PHB was dissolved in methylene chloride at 2 bar, 90° C. Equal volumes of 2% (w/w) PVP (aq) and 2% (w/w) n-OG, 1.0 mg/ml Bodipy® in TRIS-HCl buffer (10 mM, pH 8) were mixed. This solution (2 ml) was injected (during homogenisation at 20 000 rpm) to the 4 ml of methylene chloride containing 1% (w/w) PHB and 0.4% (w/w) AOT in a 25 ml Kinematica dispersion vessel. The total homogenisation time was 3 minutes. The homogenizer used was a Polytron PT3100, Rotor PT-DA 3012/2 (Kinematica AG, Switzerland). All procedures were performed under ambient conditions. Ethanol was used as a modifier (the three-component nozzle connected in a two-solutions mode) with the flow-rate 0.5 ml/min. The running conditions are presented in Table 2.

TABLE 2

SEDS processing of emulsion in example 2

| Run | P (bar) | T (° C.) | Flow rate $CO_2$ (ml/min) | Flow rate emulsion (ml/min) |
|-----|---------|----------|---------------------------|------------------------------|
| 3   | 180     | 50       | 26                        | 0.1                          |

According to SEM graphs, the particles were 1–3 lm in size.

No fluorescent substance could be traced leaving the vessel with the carbon dioxide flow.

This means that Bodipy® was not been extracted by supercritical fluid or solvents used.

EXAMPLE 3

Bodipy® in PHB, Water Content of the Emulsion: 20% (v/v)

The purpose was to associate a low molecular weight molecule to the carrier matrix (as in Example 2) using an emulsion with the water content of 20% (v/v). PHB was dissolved in methylene chloride at 2 bar, 90° C. Equal volumes of 2% (w/w) PVP (aq) and 2% (w/w) n-OG, 1.0 mg/ml Bodipy® in TRIS-HCl buffer (10 mM, pH 8) were mixed. This solution (2 ml) was injected (during homogenisation at 20000 rpm) to 8 ml of methylene chloride containing 1% (w/w) PHB and 0.4% (w/w) AOT in a 25 ml Kinematica dispersion vessel. The total homogenisation time was 3 minutes. The homogenizer used was a Polytron PT3100, Rotor PT-DA 3012/2 (Kinematica AG, Switzerland). All procedures were performed under ambient conditions.

The run 4 was done in SEDS equipment by using the three-component nozzle in the two solution mode with ethanol (flow rate 0.5 ml/min) as a modifier. In run 5 the sandwich mode was used (Table 3).

TABLE 3

SEDS processing of emulsion in example 3.

| Run | Modifier | P (bar) | T (° C.) | Flow rate $CO_2$ (ml/min) | Flow rate emulsion (ml/min) |
|---|---|---|---|---|---|
| 4 | ethanol | 180 | 50 | 26 | 0.1 |
| 5 | — | 240 | 35 | 26 | 0.1 |

Both batches have a particle size between 1–3 µm, according to SEM graphs.

The theoretical composition of particles was 55.8% (w/w) PHB, 43.5% (w/w) surfactants and 0.6% (w/w) Bodipy®. The amount of Bodipy® associated to the particles of run 5 was found to be 0.7% (w/w) according to the analysis.

EXAMPLE 4

Carbonic Anhydrase in PLG, Water Content of the Emulsion 20% (v/v)

An amount of 200 µl 20 mg/ml carbonic anhydrase (93%) in TRIS-$SO_4$ buffer (0.1 M, pH 7.5) was added to 800 µl 8% (w/w) PLG, 0.4% (w/w) Span 85/Tween 80 (80:20 weight ratio) during homogenisation with an ultrasonic probe (CV26, Sonics & Materials Inc., USA), at about 30–50 W for 3 minutes. The emulsion was prepared in a 4 ml glass vial on ice.

The running conditions for the preparation of the particles are described in Table 4. The runs were made with the three-component nozzle in the sandwich mode.

TABLE 4

SEDS processing of emulsion in example 3

| Run | P (bar) | T (° C.) | Flow rate $CO_2$ (ml/min) | Flow rate emulsion (ml/min) |
|---|---|---|---|---|
| 6 | 240 | 35 | 26 | 0.1 |

According to SEM graphs, the particles made had a particle size between 10–100 µm.

Theoretical composition of particles was 91.4% (w/w) PLG, 4.6% (w/w) surfactants and 4.0% (w/w) carbonic anhydrase. The analysis of the amount of protein gave a result of 4% (w/w) carbonic anhydrase and no protein was associated to the particle surface.

What is claimed is:

1. A process for the preparation of a formulation which comprises at least one active substance associated with a carrier comprising the steps of:
   preparing an emulsion by mixing a liquid, non-aqueous phase and a liquid, aqueous phase, the aqueous phase comprising the active substance and the carrier being present in at least one of the phases;
   contacting the emulsion with a fluid gas using an anti-solvent technique; and
   collecting units freed of liquid phase.

2. The process according to claim 1 wherein the active substance is dissolved in the aqueous phase.

3. The process according to claim 1 wherein the active substance is dispersed in the aqueous phase.

4. The process according to claim 1 wherein the active substance is solubilised in the aqueous phase.

5. The process according to any of the preceding claims wherein the active substance is a protein.

6. The process according to claim 5 wherein the active substance is an antigen.

7. The process according to claim 6 wherein the active substance is a Helicobacter antigen.

8. The process according to claim 7 wherein the active substance is a lipidated, water insoluble Helicobacter pylori adhesion protein A.

9. The process according to claim 8 wherein the active substance is the specific fully lipidated form of Helicobacter pylori adhesion protein A.

10. The process according to any one of claims 1–4 wherein the active substance is a low molecular weight substance.

11. The process according to any one of claims 1–4 wherein the non-aqueous phase contains an organic solvent.

12. The process according to any one of claims 1–4 wherein the non-aqueous phase contains a mixture of organic solvents.

13. The process according to any one of claims 1–4 wherein the aqueous phase is more polar than the non-aqueous phase.

14. The process according to any one of claims 1–4 wherein the emulsion is a macroemulsion.

15. The process according to any one of claims 1–4 wherein the emulsion is a microemulsion.

16. The process according to any one of claims 1–4 wherein the emulsion is a combination of a macroemulsion and a microemulsion.

17. The process according to any one of claims 1–4 wherein the emulsion contains an emulsifier.

18. The process according to claim 17 wherein the emulsifier is a non-ionic surfactant.

19. The process according to claim 17 wherein the emulsifier is an anionic surfactant.

20. The process according to claim 17 wherein the emulsifier is a cationic surfactant.

21. The process according to claim 17 wherein the emulsifier is a zwitterionic surfactant.

22. The process according to claim 17 wherein the emulsifier is a polymer.

23. The process according to claim 17 wherein the emulsifier is a lipid.

24. The process according to any one of claims 1–4 wherein the carrier is poly(3-hydroxybutyrate).

25. The process according to any one of claims 1–4 wherein the carrier is poly(DL-lactic-co-glycolic acid).

26. The process according to any one of claims 1–4 wherein the emulsion is contacted with a fluid gas by the use of a fluid gas technique.

27. The process according to claim 26 wherein the employed fluid gas technique is SEDS.

28. The process according to claim 26 wherein the employed fluid gas technique is ASES.

29. The process according to claim 26 wherein the employed fluid gas technique is SAS.

30. The process according to claim 26 wherein the employed fluid gas technique is GAS.

31. The process according to claim 26 wherein the employed fluid gas technique is PCA.

32. The process according to any one of claims 27–31 wherein the fluid gas is carbon dioxide.

33. The process according to claim 26 wherein the fluid gas is carbon dioxide.

34. A formulation prepared as described in any one of claims 1–4, 6–9, 18–23, 27–31, and 33.

35. A formulation prepared as described in claim 5.

36. A formulation prepared as described in claim 10.

37. A formulation prepared as described in claim 24.

38. A formulation prepared as described in claim 25.

39. A formulation prepared as described in claim 26.

40. A formulation prepared as described in claim 32.

41. A process for the preparation of a formulation which comprises at least one active substance associated with a carrier comprising the steps of:

preparing an emulsion by mixing a liquid, non-aqueous phase and a liquid, aqueous phase, the aqueous phase comprising the active substance and the carrier being present in at least one of the phases;

freeing the active substance associated with the carrier from the liquid phases by contacting the emulsion with a fluid gas using an anti-solvent technique selected from the group consisting of SEDS, ASES, SAS, GAS and PCA; and collecting the freed units of the active substance associated with the carrier.

* * * * *

UNITED STATES PATENT AND TRADEMARK OFFICE
CERTIFICATE OF CORRECTION

PATENT NO. : 6,372,260 B1
DATED : April 16, 2002
INVENTOR(S) : Andersson et al.

It is certified that error appears in the above-identified patent and that said Letters Patent is hereby corrected as shown below:

<u>Title page,</u>
Item [*] Notice, "Subject to any disclaimer, the term of this patent is extended or adjusted under 35 USC 154(b) by (73) days", delete the phrase by "73 days" and insert -- by 0 days --

Signed and Sealed this

Fourteenth Day of October, 2003

JAMES E. ROGAN
*Director of the United States Patent and Trademark Office*